(12) United States Patent
Taniwaki et al.

(10) Patent No.: US 10,517,825 B2
(45) Date of Patent: Dec. 31, 2019

(54) POWDER COMPOSITION CONTAINING OILY SUBSTANCE

(71) Applicant: TOMITA PHARMACEUTICAL CO., LTD., Naruto-shi, Tokushima (JP)

(72) Inventors: Takanori Taniwaki, Naruto (JP); Kazuki Kamai, Naruto (JP); Yuuta Tsumura, Naruto (JP); Daichi Masaki, Naruto (JP)

(73) Assignee: TOMITA PHARMACEUTICAL CO., LTD., Naruto-shi (JP)

( * ) Notice: Subject to any disclaimer, the term of this patent is extended or adjusted under 35 U.S.C. 154(b) by 0 days.

(21) Appl. No.: 15/578,113

(22) PCT Filed: May 27, 2016

(86) PCT No.: PCT/JP2016/065700
§ 371 (c)(1),
(2) Date: Nov. 29, 2017

(87) PCT Pub. No.: WO2016/194805
PCT Pub. Date: Dec. 8, 2016

(65) Prior Publication Data
US 2018/0153809 A1 Jun. 7, 2018

(30) Foreign Application Priority Data

May 30, 2015 (JP) ................. 2015-1109770

(51) Int. Cl.
| | | |
|---|---|---|
| *A61K 9/14* | (2006.01) | |
| *A61K 47/02* | (2006.01) | |
| *A61K 9/20* | (2006.01) | |
| *A61K 31/202* | (2006.01) | |
| *C01B 33/24* | (2006.01) | |
| *A61K 8/25* | (2006.01) | |
| *A61K 8/02* | (2006.01) | |
| *A61K 33/06* | (2006.01) | |
| *A61K 35/60* | (2006.01) | |
| *A61Q 19/00* | (2006.01) | |

(52) U.S. Cl.
CPC ............ *A61K 9/143* (2013.01); *A61K 8/0279* (2013.01); *A61K 8/25* (2013.01); *A61K 9/14* (2013.01); *A61K 9/20* (2013.01); *A61K 9/2009* (2013.01); *A61K 31/202* (2013.01); *A61K 33/06* (2013.01); *A61K 35/60* (2013.01); *A61K 47/02* (2013.01); *A61Q 19/00* (2013.01); *C01B 33/24* (2013.01); *C01P 2004/61* (2013.01); *C01P 2006/14* (2013.01)

(58) Field of Classification Search
None
See application file for complete search history.

(56) References Cited

U.S. PATENT DOCUMENTS

| | | | | |
|---|---|---|---|---|
| 8,679,547 B2* | 3/2014 | Konishi | ................. | A61K 33/06 |
| | | | | 423/331 |
| 8,980,330 B2* | 3/2015 | Konishi | ................. | A61K 33/06 |
| | | | | 423/326 |
| 2010/0028459 A1* | 2/2010 | Kis | ........................ | A61K 31/07 |
| | | | | 424/618 |
| 2013/0101685 A1* | 4/2013 | Konishi | ................. | A61K 33/06 |
| | | | | 424/682 |

FOREIGN PATENT DOCUMENTS

WO      WO2015/151997      * 10/2015

* cited by examiner

*Primary Examiner* — Katherine Peebles
(74) *Attorney, Agent, or Firm* — Locke Lord LLP; James E. Armstrong, IV; Nicholas J. DiCeglie, Jr.

(57) ABSTRACT

Provided is a powder composition containing an oily substance, the powder composition having good oxidation stability and excellent compression moldability. The powder composition containing an oily substance contains a powdery calcium silicate-based material, and an oily substance impregnated into the material. In the material, a cumulative pore volume for a pore size of 10 to 70 nm is 1.1 cc/g or more, and a cumulative pore volume for a pore size of 70 to 500 nm is 2.0 cc/g or less.

5 Claims, 1 Drawing Sheet

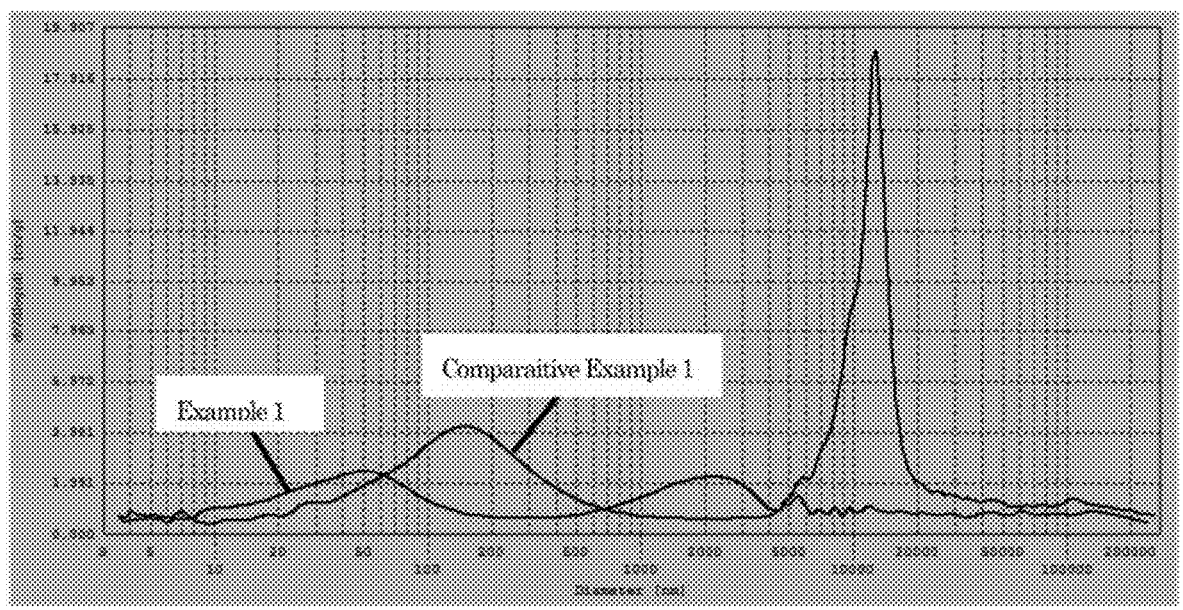

POWDER COMPOSITION CONTAINING OILY SUBSTANCE

CROSS-REFERENCE TO RELATED APPLICATIONS

The present application claims the benefit of International Application No. PCT/JP2016/065700, filed May 27, 2016, which claims priority to Japanese Application No. 2015-110970, filed May 30, 2015, the disclosures of which are incorporated herein by reference.

BACKGROUND

The present invention relates to a novel powder composition containing an oily substance.

The physiological action of components contained in fish oil collected from fish such as bonito and sardines has attracted attention. For instance, ω-3 polyunsaturated fatty acids (eicosapentaenoic acid (EPA), docosahexaenoic acid (DHA) and the like) are deemed to have potential in preventing adult diseases, through daily intake of these fatty acids. Therefore, with a view to utilizing the functionality of oily components such as highly unsaturated fatty acids, numerous compositions containing such acids have been developed in recent years.

In the field of drugs, foodstuffs and the like, for instance, there are widely used soft capsules directly filled with fish oil, using a coating film of gelatin or the like. However, a phenomenon (blocking) whereby soft capsules become adhered to each other is prone to occur as air temperature or humidity increases; moreover, contents exhibit browning and deterioration due to interactions between the contents and the coating film, giving rise to the problem of impaired storability.

Such being the case, a method has been proposed that involves supporting a functional substance, being an oily liquid or a low-melting point solid, onto a carrier made up of porous calcium silicate, to yield a powder that is then granulated, through addition of a water-soluble antioxidant and a granulation component, to produce as a result oily substance-containing granules having excellent stability (Patent document 1).

As a method for producing oily substance-containing tablets, other methods have been proposed in which the phenomenon of sticking during tableting is suppressed through the use of a solid preparation that is produced by thoroughly drying an adsorbent having an oily substance adsorbed thereon, followed by covering the dry adsorbent with an appropriate coating base material such as a sugar (Patent document 2).

A further proposed method involves using a porous calcium silicate powder as an excipient, and allowing an oily substance, or a liquid substance or a low-melting point substance derived from natural products, to be adsorbed onto and supported on the porous calcium silicate, in a state where the foregoing substance is dissolved or dispersed in an organic solvent, and adding then a starch or sugar to the whole, with compression-molding and tableting of the formed granules, to suppress as a result the phenomenon of sticking during tableting and achieve good tablet hardness (Patent document 3).

CITATION LIST

Patent Literature

[Patent document 1] WO 2009/044854
[Patent document 2] Japanese Patent Application Publication No. 2009-84205
[Patent document 3] WO 2007/097333

SUMMARY

Technical Problem

However, these conventional oily substance-containing powders are not found to be sufficient as regards oxidation stability (oxidation resistance or anti-oxidant properties). Moreover, in a case where the powders contain a large amount of oil components, a molded body (for instance granules (granulated material), tablets and the like) obtained through compression molding of the oily substance-containing powder exhibits low hardness, and further improvements are thus required also in this regard.

Generally, tablets and the like constitute widely used dosage forms, from prescription drugs to marketed drugs, in various supplements (functional foods, nutrients and the like) and also drugs, given that tablets and the like are comparatively simple to manipulate and to ingest, and the dosage thereof simple to optimize, as compared with dosage forms such as capsules and powders (ungranulated products).

To produce oily substance-containing tablets that contain an oily substance such as fish oil, methods in which for instance the oily substance is adsorbed onto an oil-absorbing carrier, followed by tableting through compression molding are ordinarily employed. In conventional techniques, however defective tableting in the form of lamination or the like occurs readily, and ever more conspicuously as the content of the oily substance increases. Lamination is herein a phenomenon whereby tablets flake off in layers due to unbalanced application of tableting pressure. Lamination is deemed to occur due to seeping of the oily component out of an oil-absorbing carrier, during compression molding, which hinders bonding of particles to one another.

The occurrence of lamination translates not only into appearance defects but also into non-uniform distribution of the oily substance that is contained. Disintegratability in the body after ingestion, as well as leachability and so forth become inappropriate, which significantly detracts from the value of the product. Moreover, the drop in hardness of the tablets or the like incurred as a result makes for likelier breakage or chipping of the tablets during transport or when removed from PTP packing.

Therefore, an object of the present invention is to provide a powder composition containing an oily substance, the powder composition having good oxidation stability and excellent compression moldability.

Solution to Problem

As a result of diligent research conducted in the light of conventional problems, the inventors found that the above goal can be attained by impregnating an oily substance into a powdery calcium silicate-based material having a specific pore structure, and perfected the present invention on the basis of that finding.

Specifically, the present invention relates to the powder composition containing an oily substance below.

1. A powder composition containing an oily substance, the powder composition containing a powdery calcium silicate-based material, and an oily substance impregnated into the material, wherein, in the material, a cumulative pore volume for a pore size of 10 to 70 nm is 1.1 cc/g or more and a cumulative pore volume for a pore size of 70 to 500 nm is 2.0 cc/g or less.

2. The powder composition containing an oily substance according to 1, wherein the oily substance is at least one type from among 1) a component of at least one of docosahexaenoic acid (DHA) and eicosapentaenoic acid (EPA), 2) an edible natural oil containing the component, and 3) a refined oil of the edible natural oil.

3. The powder composition containing an oily substance according to 1 or 2, having an average particle diameter of 1 to 50 μm.

4. The composition containing an oily substance according to any one of 1 to 3, wherein the content of the oily substance is 30 wt % or higher.

5. A molded body obtained through compression molding of the composition containing an oily substance according to any one of 1 to 4.

Advantages of Invention

In the powder composition containing an oily substance of the present invention, an oily substance is supported on calcium silicate having a specific pore structure, and hence it becomes possible to bring out good moldability along with excellent stability to oxidation. Lamination and the like caused for instance by seepage of the oily substance can be prevented effectively as a result.

Regarding oxidation resistance, when allowing an oily substance to adsorb onto an oil-absorbing carrier, the oily substance becomes generally held on the surface of particles of the oil-absorbing carrier and inside the pores of the oil-absorbing carrier. In this case the oily substance held on the particle surface is oxidized easily in environments where the oily substance is constantly in contact with air. By contrast, the oily substance held inside the pores is not oxidized readily, and can be held stably over a prolonged period of time.

In the present invention, a greater amount of oily substance can be held in the pores through the use of an oil-absorbing carrier in the form of a calcium silicate-based material having a specific pore structure. The oily substance becomes protected as a result from oxidation, and can be held stably over a prolonged period of time.

Regarding moldability, it is found that in a case where compression molding is attempted on a powder composition containing an oily substance, bonding of particles to one another is hindered by the oily substance held on the particle surface, and defects occur such as lamination and a reduction in molded body hardness. During compression molding, pores of comparatively large pore size collapse readily, while pores of small pore size retain their shape. It is accordingly deemed, from a micro viewpoint, that when the oily substance is supported at a high content, the oily substance held in pores of comparatively large pore size seeps out from pores and hinders bonding of particles to one another, giving rise to defects such as lamination and decreased molded body hardness. By contrast, pores having a comparatively small pore size retain their shape, and accordingly the oily substance maintained in the pores of small pore size does not seep out readily. Thus, in the present invention, a significant amount of oily substance can be maintained in small pores that do not collapse during compression molding, by using a calcium silicate-based material having a specific pore structure. It is found that a molded body (oily substance-containing granules or tablets) can be provided as a result that exhibits high molded body hardness without defects such as lamination.

BRIEF DESCRIPTION OF DRAWING

FIG. 1 is a diagram illustrating the results of a pore distribution measurement, according to a mercury intrusion technique, of powders having no oily substance supported thereon, in Example 1 and Comparative example 1.

DETAILED DESCRIPTION

1. Powder Composition Containing an Oily Substance

The powder composition containing an oily substance of the present invention (composition of the present invention) is a powder composition that contains a powdery calcium silicate-based material, and an oily substance impregnated into the material, wherein, in the material, a cumulative pore volume for a pore size of 10 to 70 nm is 1.1 cc/g or more, and a cumulative pore volume for a pore size of 70 to 500 nm is 2.0 cc/g or less.

Regarding the pore structure of the calcium silicate-based material, the cumulative pore volume for a pore size of 10 to 70 nm is ordinarily 1.1 cc/g or more, and lies preferably within the range of 1.1 to 2.0 cc/g, more preferably 1.1 to 1.5 cc/g. The cumulative pore volume for a pore size of 70 to 500 nm is ordinarily 2.0 cc/g or less, and lies preferably within the range of 0.6 to 1.0 cc/g, more preferably 0.6 to 0.8 cc/g.

In the composition of the present invention, thus, a calcium silicate-based material the cumulative pore volume of which for a pore size of 10 to 70 nm is 1.1 cc/g or more while the cumulative pore volume for a pore size of 70 to 500 nm is 2.0 cc/g or less, is used as a liquid-absorbing carrier. As a result, the oily substance is held stably inside the pores, and pores do not break readily during compression molding, which in turn allows providing oily substance-containing granules or tablets having good molded body hardness and in which defects do not occur readily during molding.

In the composition of the present invention, the calcium silicate-based material is used as an oil-absorbing carrier, and hence the oil absorption is preferably higher. For example, the oil absorption is 2.5 mL/g or greater, more preferably 2.7 mL/g or greater. Specifically, the material of the present invention having a prescribed pore volume allows achieving a high oil absorption and increasing the content of the oily substance, thanks to the pore structure of the material.

The specific surface area of the calcium silicate-based material is not limited, but is preferably higher. For instance the BET specific surface area is ordinarily about 50 to 400 $m^2/g$, and particularly preferably 100 to 400 $m^2/g$. A higher oil absorption characteristic can be thus obtained by employing such high specific surface area.

The calcium silicate-based material takes on a powdery form, with the appearance of a dry powder. The average particle diameter of the calcium silicate-based material can be set as appropriate for instance in accordance with the application and method of use of the material of the present invention, but is normally set to about 1 to 100 μm, in particular to 1 to 50 μm, and yet more preferably to 5 to 25 μm, for instance in terms of compression moldability.

The content of the calcium silicate-based material of the composition of the present invention is not limited, but is ordinarily set to about 20 to 70 wt %, particularly preferably to 40 to 50 wt %. As a result it becomes possible to hold the oily substance yet more effectively on the calcium silicate-based material.

In the composition of the present invention, the oily substance is impregnated into the calcium silicate-based material. Specifically, the oily substance is supported on the calcium silicate-based material serving as a carrier (oil-absorbing carrier). Before intake of the composition of the present invention, therefore, the oily substance is confined and immobilized within the calcium silicate-based material (in particular, inside the pores). The oily substance however dissolves in the body after ingestion of the composition.

The oily substance may be any natural product or synthetic product, so long as the substance is edible. The term oily substance also encompasses for instance oils (fats and oils), lipophilic substances and the like. In the present invention, there can be suitably used in particular at least one type from among 1) edible natural oils, 2) refined oils of the edible natural oils, and 3) extracted components of the foregoing oils. Examples of natural oils include for instance animal oils such as fish oil (bonito oil, saury oil, sardine oil, mackerel oil and the like), beef oil, whale oil and the like, and vegetable oils such as soybean oil, sesame oil, perilla oil, rapeseed oil and linseed oil. Examples of phospholipid-rich oils include for instance lecithin, lecithin-rich oil, krill oil and the like.

Specific components of the oily substance include for instance lipophilic substances such as vitamin A, vitamin A derivatives, vitamin E, vitamin D, vitamin K, docosahexaenoic acid (DHA), eicosapentaenoic acid (EPA), β-carotene, lutein, astaxanthin, lycopene, lipoic acid, linoleic acid, α-linolenic acid, γ-linolenic acid, and tocotrienols.

In the present invention, in particular, at least one type of 1) a component of at least one of docosahexaenoic acid (DHA) and eicosapentaenoic acid (EPA), 2) an edible natural oil containing the component, and 3) a refined oil of the edible natural oil can be suitably used as the oily component.

The form of the oily substance that is used in the present invention is ordinarily liquid; it suffices herein that the viscosity thereof (25° C.) be within the range of about 10 to 1000 mPa·s. In the present invention, such a liquid oily substance is impregnated into a calcium silicate-based material and is held inside pores. As a result, it becomes possible to obtain a composition of powdery (dry powdery) appearance.

The content of the oily substance in the composition of the present invention is not limited, and may be ordinarily 30 wt % or higher, and is particularly preferably set to 30 to 80 wt %, yet more preferably to 50 to 60 wt %. In the present invention, in particular, for instance 100 to 130 parts by weight of oily substance can be effectively supported on 100 parts by weight of the calcium silicate-based material, as illustrated in the examples.

Other components may be added as needed to the composition of the present invention as long as they do not substantially adversely affect the advantages of the present invention. Examples of additives include for instance common excipients such as cellulose and sugars, disintegrants such as croscarmellose sodium, fluidizing agents such as anhydrous silicic acid, and lubricants such as calcium stearate, as well as moisture-proof agents, stabilizers, binders and the like. A coating of a sugar or the like may be provided for the purpose of leaching control and bitterness mitigation, among others.

2. Production of a Powder Composition Containing an Oily Substance

For example, a method for producing the composition of the present invention can be realized in the form of a production method that comprises (A) a step of preparing a calcium silicate-based material (preparation step) and (B) a step of impregnating (supporting) an oily substance into the calcium silicate-based material (impregnation step). More specifically, the composition of the present invention can be suitably produced in particular in accordance with the production method below.

(A) Preparation Step

In the preparation step, a powdery calcium silicate-based material is prepared in accordance with a method as follows. This method allows obtaining more reliably a powdery calcium silicate-based material having a predetermined pore structure.

Specifically, a powdery calcium silicate-based material can be prepared suitably by a calcium silicate-based material production method having:

(1) a first step of obtaining a first aqueous slurry containing a first reaction product by adding an alkali to a calcium-containing solution resulting from dispersing or dissolving a calcium starting material in an aqueous medium to allow them to react with each other;

(2) a second step of obtaining a second aqueous slurry containing a second reaction product by adding a silicic acid starting material to the first aqueous slurry or in an aqueous slurry resulting from adjusting the water content of the first aqueous slurry to allow them to react with each other;

(3) a third step of obtaining a third aqueous slurry containing a calcium silicate-based material by adjustment of the pH of the second aqueous slurry or of an aqueous slurry resulting from adjusting the water content of the second aqueous slurry. The various steps are explained next.

First Step

In the first step, there is obtained a first aqueous slurry containing a first reaction product, by eliciting a reaction, through addition of an alkali, in a calcium-containing liquid resulting from dispersing or dissolving a calcium starting material in an aqueous medium.

The calcium-containing liquid used in the first step is prepared for instance by dispersing or dissolving a calcium starting material in an aqueous medium.

The calcium starting material is not limited, and known calcium sources identical to those used for producing calcium silicate can be used herein. Examples of water-soluble calcium starting materials include calcium chloride, calcium nitrate, and the like, as well as water-soluble calcium salts of organic acids. Examples of calcium starting materials that are insoluble or poorly soluble in water include calcium oxide, calcium hydroxide, calcium carbonate, calcium sulfate and insoluble calcium salts of organic acids. In the present invention, there can be suitably used, in particular, at least one type of calcium starting material from among calcium chloride, calcium nitrate, calcium hydroxide, calcium oxide and the like, in terms of conducting the reaction with the silicic acid starting material in a specific manner thanks to the co-presence of calcium hydroxide and calcium ions in the reaction solution.

The calcium-containing liquid may be any one of 1) a solution (i.e. a solution containing calcium ions) in which a calcium starting material is dissolved in an aqueous medium, 2) a dispersion in which a calcium starting material is dispersed in an aqueous medium, or 3) a mixed solution containing calcium ions and a calcium starting material dispersed in an aqueous medium, for example.

At least one of water and a water-soluble organic solvent can be suitably used as the aqueous medium. As the water-soluble organic solvent, for example, there can be utilized an alcohol such as methanol, ethanol and propanol as well as acetone or the like. In the present invention, water is used particularly preferably.

The concentration of the calcium starting material in the calcium-containing liquid is not particularly limited, but ordinarily the liquid is prepared as appropriate in such a manner that the solids concentration of the calcium starting material is 1 to 30 wt %, preferably about 1 to 20 wt %.

The alkali is not limited, and examples thereof include sodium hydroxide, potassium hydroxide, ammonia, ammonium salts, aqueous ammonia and the like. In particular at least one of sodium hydroxide and potassium hydroxide can be used suitably. The addition amount of alkali is preferably adjusted so that the pH is 8.0 to 13.0, in particular 11.0 to 12.5. Through addition of an alkali so that pH takes on such values it becomes possible to obtain suitably the first aqueous slurry containing calcium hydroxide as the first reaction product. In particular, calcium ions derived from a soluble calcium starting material and calcium hydroxide (solid calcium compound) generated through reaction with an alkali are preferably co-present in the first aqueous slurry.

Second Step

In the second step, there is obtained a second aqueous slurry containing a second reaction product by eliciting a reaction, through addition of a silicic acid starting material, in the first aqueous slurry or in an aqueous slurry resulting from adjusting the water content of the first aqueous slurry.

In the second step, it is preferable to use the first aqueous slurry obtained in the first step as-is without adjustment of the water content, but an aqueous slurry resulting from adjusting the water content of the first aqueous slurry can also be used, as needed.

Preferably, calcium ions from a soluble calcium source and solid calcium from calcium hydroxide generated through reaction with an alkali are co-present in the first aqueous slurry. By virtue of the co-presence of calcium ions and solid calcium in the first aqueous slurry it becomes possible to influence reactivity with the silicic acid starting material and the pore structure of the reaction product, and to effectively obtain a porous reaction product.

As the silicic acid starting material there can be used known starting materials identical to those used for producing known calcium silicate. Examples thereof include silicon dioxide, sodium silicate, potassium silicate, silica sol and the like. In particular, there can be suitably used at least one type from among silicon dioxide, sodium silicate and the like.

The addition amount of the silicic acid starting material is set so that there is generated a predetermined calcium silicate. Specifically, the addition amount may be set so that the $SiO_2/CaO$ molar ratio theoretically lies within the range of 1.5 to 6.5, more preferably within the range of 1.5 to 5.0.

The silicic acid starting material is caused to react by being mixed with the first reaction product. A second reaction product containing calcium silicate can be obtained as a result. The second reaction product can be ordinarily generated in the form of an aqueous slurry. The reaction temperature is not particularly limited, but is for instance 5° C. to 100° C., and in particular is preferably set, as appropriate, to lie within the range of 70° C. to 80° C. The atmosphere (atmospheric pressure) may serve as the reaction atmosphere. The reaction time can be adjusted as appropriate in accordance with the reaction temperature, for example. The production method of the present invention allows thus obtaining the second reaction product under comparatively mild conditions, without relying on hydrothermal synthesis reactions (autoclave).

Aging Step

In the present invention, preferably, the second aqueous slurry or aqueous slurry resulting from adjusting the water content of the second aqueous slurry, is subjected beforehand to an aging step prior to the third step, as needed. Performing an aging step allows promoting the reaction of unreacted calcium, and promoting more effectively formation of a pore structure. Such being the case, the aging step is preferably carried out while under stirring of the second aqueous slurry. The aging temperature is not limited, but in general is preferably set to 50° C. to 70° C., and more preferably, in particular, to 55° C. to 65° C. The aging time is not particularly limited, and may be usually set to 0.5 to 10 hours, preferably 1 to 1.5 hours. The solids concentration of the second aqueous slurry during the aging step is not particularly limited, but is ordinarily set to 1 to 30 wt %, more preferably to about 3 to 20 wt %.

Third Step

In the third step, there is obtained a third aqueous slurry containing a calcium silicate-based material, through adjustment of the pH of the second aqueous slurry or of an aqueous slurry resulting from adjusting the water content of the second aqueous slurry.

In the third step, it is preferable to use the second aqueous slurry obtained in the second step as-is, without adjustment of the water content, but an aqueous slurry resulting from adjusting the water content of the second aqueous slurry can be used if necessary.

Adjustment of the pH is not particularly limited, and may be accomplished so that a predetermined calcium silicate-based material is formed out of the above aqueous slurry. Examples of pH regulators that can be used include acids (hydrochloric acid, nitric acid, sulfuric acid, organic acids and the like) as well as alkalis (sodium hydroxide and the like), for instance. In the present invention, in particular, the pH is adjusted to about 7.0 to 11.0, and particularly preferably to pH 8.0 to 10.9. By adjusting the pH so as to lie within such a range, the silicon dioxide present dissolved in an aqueous solvent is caused to precipitate, calcium in the calcium silicate is dissolved partially by an acid, and it becomes thus possible to prepare mixed crystals of silicon dioxide/calcium silicate. As a result there can be obtained a third aqueous slurry comprising particles of calcium silicate-based material dispersed therein.

Solid-Liquid Separation Step, Water Washing Step and so Forth

In the present invention, the third aqueous slurry can be used, as-is, as a starting material for various applications; however, the third aqueous slurry may be subjected to a solid-liquid separation step, a water washing step, a drying step, a grinding step, a classification step or the like, as needed.

The solid-liquid separation step can be carried out through dewatering, for instance by ordinary filtration such as pressure filtration, reduced-pressure filtration, vacuum filtration, natural filtration, and centrifugal filtration. Known or commercially available equipment, for instance a filter press, a centrifuge or the like can be used herein.

The water washing step may involve washing with water the solids obtained in the solid-liquid separation step. Water washing may be carried out to an extent such that the electric conductivity of the washing filtrate is brought to 200 to 300 μS/cm, preferably 200 to 250 μS/cm.

The drying step may be either natural drying or heat drying; in the case of heat drying, the temperature may be set ordinarily within a temperature range of about 60° C. to 120° C. Preferably, the drying method involves drying under conditions such that substantially no shear forces are exerted. For instance a drying method such as static drying, instant drying, spray drying, freeze drying, vacuum drying or microwave drying can be preferably employed.

The grinding step may be a method in which impurities are unlikely to become mixed in and for example a known grinding method of shear type, disc type, roller type, cylinder type, impact type, jet type, high-speed rotary type or the like can be employed. The means involved in the classification step are not limited, and a known method such as screening and air classification which is dry sieving methods, can be employed.

(B) Impregnation Step

In the impregnation step, an oily substance is impregnated into (supported on) the calcium silicate-based material having been obtained in step (A). The various substances mentioned above can be used as the oily substance for impregnation.

The method for impregnating the oily substance is not particularly limited, and impregnation can be accomplished for instance by adding the oily substance to a powdery calcium silicate-based material and then stirring. The addition method in this case is not limited, and any method can be employed among 1) direct addition and 2) dispersing or dissolving the oily substance in a solvent in advance and followed by addition.

The solvent is not particularly limited, so long as the oily substance (oil-soluble solvent) can be dissolved thereby. The solvent can be decided upon as appropriate taking into consideration for instance the type of the oily substance that is used. Examples of organic solvents include alcohols such as ethanol, propanol, methanol and the like, as well as chloroform, acetone, dimethyl sulfoxide, diethyl ether, dichloromethane, and ethyl acetate. Alcohols such as ethanol and propanol are high volatile and highly safe, and are therefore preferably used herein.

In a case where the normal-temperature viscosity of the oily substance that is used is comparatively high, impregnation of the oily substance into the powdery calcium silicate-based material can be promoted by lowering the viscosity through heating within a temperature range lower than the boiling point of the oily substance.

3. Molded Body

The present invention encompasses a molded body obtained through compression molding of the powder composition containing an oily substance. The compression molding method is not particularly limited, and may be for instance press molding (including tableting), as well as granulation under pressure. Compression molding may be of dry type or of wet type.

As a result, molded bodies of tablet type or granule type can be suitably used in the present invention, and the molded bodies can be obtained through tableting or granulation, using a commercially available tableting machines or granulators. For example, to produce for instance a molded body of tablet type, the compression pressure during tableting in a tableting machine may be set as appropriate in accordance with the formulation of the composition of the present invention and the desired hardness of the tablets for example, but ordinarily it suffices to perform tableting at a compression pressure within the range of 3 to 20 kN. In the composition of the present invention, defective tableting such as lamination is effectively suppressed, even for high compression pressure, and accordingly it becomes possible to provide efficiently oily substance-containing granules and tablets having for instance sufficient hardness (for example, 40 N or greater, and preferably 50 N or greater, in the case of tablets).

EXAMPLES

The features of the present invention will be explained next more specifically by way of examples and comparative examples. The scope of the present invention is however not limited to the examples. In the disclosure of the examples, "%" signifies "wt %".

Example 1

Herein 2500 kg of water were charged into a reactor, and liquid temperature was raised to 72.5° C. Then 250 kg of calcium chloride were charged, and the calcium chloride was dissolved completely. Next, 136 kg of a 48% sodium hydroxide liquid were adjusted to 240 L with water and then the obtained solution was dropped into the reactor over 30 minutes. Once dropping was over, 520 L of #3 sodium silicate were adjusted to 2000 L with water and then the solution was dropped into the reactor over 3 hours. Thereafter, the liquid temperature was brought to 60° C., and aging was carried out for 1 hour. After aging was over, the pH of the reaction product was adjusted to 9.0 using 18% hydrochloric acid. Next, washing with water was performed using a filter press, and was continued until a conductivity of 250 μS/cm reached. Then, water was added to the obtained aqueous cake, to prepare an aqueous slurry having 7 wt % solids. This slurry was spray-dried using a disk dryer of a spray drier (ODT-62 model spray dryer: Ohkawara Kakohki Co., Ltd.), at an inlet temperature of 400° C., outlet temperature of 170° C., and disk rotational speed of 10,000 rpm. A powder of a calcium silicate-based material was then obtained as a result of a grinding step of the powder recovered from the chamber and from the cyclone of the spray dryer.

Then 30 g of bonito fish oil were added, at room temperature, to 30 g of the powder of a calcium silicate-based material thus obtained, followed by kneading for 5 minutes using a desk crusher Milser 800DG (by Iwatani Corporation), to thereby cause the fish oil to be supported on the calcium silicate-based material, and yield a powder composition containing an oily substance.

Example 2

A sample was prepared, and a powder composition containing an oily substance obtained, in the same way as in Example 1, but with the amount of added fish oil set herein to 39 g.

Example 3

A sample was prepared, and a powder composition containing an oily substance obtained, in the same way as in Example 1, but herein the rotational speed of the disk of the spray drier was set to 8000 rpm, with recovery only in the chamber of the spray drier.

Example 4

A sample was prepared, and a powder composition containing an oily substance obtained, in the same way as in Example 1, but herein the rotational speed of the disk of the spray drier was set to 12,000 rpm, and recovery was conducted in the chamber and in the cyclone of the spray drier.

Comparative Example 1

A sample was prepared, and a powder composition containing an oily substance obtained, in the same way as in Example 1, but herein "FLORITE R" Lot No: H5026R by Tomita Pharmaceutical Co., Ltd. was used as a commercially available calcium silicate-based material.

Comparative Example 2

A sample was prepared, and a powder composition containing an oily substance obtained, in the same way as in Comparative example 1, but with the amount of added fish oil set herein to 39 g.

Comparative Example 3

A sample was prepared, and a powder composition containing an oily substance obtained, in the same way as in Example 1, but herein "NF calcium silicate" Lot No: H30306, by Tomita Pharmaceutical Co., Ltd., was used as a commercially available calcium silicate-based material.

Comparative Example 4

A sample was prepared, and a powder composition containing an oily substance obtained, in the same way as in Example 1, but herein "AEROSIL 200" Lot No: 614020181, by Evonik Degussa Corporation, was used as a commercially available silicon dioxide-based material.

Test Example 1

The cumulative pore volume, oil absorption, specific surface area and average particle size of each sample before supporting fish oil, in Examples 1, 3 and 4 and Comparative examples 1, 3 and 4, were measured herein. The results are given in Table 1.

(1) Cumulative Pore Volume

Measurements were performed under the conditions below, using a mercury porosimeter ("Poremaster 60GT" by Quantachrome Corporation). Herein 0.05 g of each sample were sealed in a measurement cell, the contact angle of mercury was set to 1400, the surface tension of mercury was set to 480 dyn/cm, and the cumulative pore volume was calculated on the basis of the measured pressure. The analysis ranges herein were set to pore size from 10 to 70 nm and pore size from 70 to 500 nm.

(2) Oil Absorption

Herein 1.0 g of sample is weighed and placed on a black plastic plate. Then trickles of 4 or 5 drops of boiled linseed oil held in a burette are dropped from above, while thoroughly kneading the drops with the powder using a spatula. Once the whole became a hard putty-like mass, kneading was performed accompanying each drop, and dropping was terminated just before sudden softening with the last drop. The dropping amount of boiled linseed oil at that time was read, and the oil absorption was calculated on the basis of the following expression.

Oil absorption (mL/g)=volume of dropped boiled linseed oil (mL)/sample mass (g)

(3) BET Specific Surface Area

The BET specific surface area was measured under the operating conditions below, using a high-speed specific surface area pore distribution measuring device ("Nova-4000e", by Quantachrome Corporation).

Pretreatment conditions: herein 0.02 g of sample were accurately weighed and were sealed in an adsorption pipe that was then degassed for 1 hour at 105° C.

Measurement and analysis: adsorption isotherms of nitrogen gas at the liquid nitrogen gas temperature were worked out, and the BET specific surface area was calculated in accordance with a multipoint BET method, for relative pressures of 0.1, 0.2 and 0.3.

(4) Average Particle Diameter

A sample was subjected to ultrasonic agitation (ultrasonic output 40 W) for 3 minutes, was thereafter dispersed in water, and the average particle size in the water solvent was measured by laser diffraction. The measuring device used herein was "Microtrac MT3300EX II" by MicrotracBEL Corp.

TABLE 1

|  | Cumulative pore volume (cc/g) | | Oil absorption (mL/g) | Specific surface area (m$^2$/g) | Average particle diameter (μm) |
| --- | --- | --- | --- | --- | --- |
|  | 10 to 70 nm | 70 to 500 nm |  |  |  |
| Example 1 | 1.42 | 0.62 | 3.9 | 304.0 | 9.3 |
| Example 3 | 1.36 | 0.74 | 3.1 | 214.0 | 9.3 |
| Example 4 | 1.18 | 0.73 | 3.5 | 270.0 | 9.6 |
| Comp. ex. 1 | 0.91 | 2.23 | 4.6 | 133.0 | 28.3 |
| Comp. ex. 3 | 1.01 | 0.41 | 2.7 | 172.2 | 22.8 |
| Comp. ex. 4 | 1.04 | 0.81 | 2.5 | 187.3 | 20.4 |

The results in Table 1 and FIG. 1 reveal that in the samples without oily substance supported thereon, in Examples 1, 3 and 4, the cumulative pore volume for a pore size of 10 to 70 nm reaches 1.1 cc/g or more, while the cumulative pore volume for a pore size of 70 to 500 nm is small, of 2.0 cc/g or less.

Test Example 2

The average particle size of the samples obtained in Examples 1 to 4 and Comparative examples 1 to 4 was measured in accordance with the measurement method in (4) of Test example 1 above. Moreover, oxidation stability over 3 days and 7 days in a storage environment at 40° C. was measured in accordance with the measurement method below. The result for 0 days refers to the peroxide value (POV) in (6) for fish oil before being supported. The results are given in Table 2.

(5) Extraction of Oil from a Powder Composition

Herein 30 g of a powder composition containing an oily substance were measured in a beaker, enough diethyl ether was added so as to sufficiently wet the sample, and the sample was left to soak, under occasional stirring, for about 30 minutes. After the sample had been allowed to stand, the resulting diethyl ether layer was separated and filtered. The solvent was distilled off under reduced pressure, at or below 40° C., and the obtained oily substance was used as a test solution.

(6) Peroxide Value

The peroxide value (POV) of the oily substance obtained in (5) was measured, as an indicator of oxidation stability. The POV measurement was conducted on the basis of the chloroform method set forth in the "Standard methods for the analysis of fats, oils and related materials, 2003 edition" of the Japan Oil Chemists' Society.

TABLE 2

|  | Average particle diameter (μm) | POV after storage at 40° C. (meq/kg) | | |
| --- | --- | --- | --- | --- |
| | | 0 days | 3 days | 7 days |
| Example 1 | 9.5 | 6.8 | 3.8 | 7.3 |
| Example 2 | 9.3 | 6.8 | 5.2 | 8.9 |
| Example 3 | 9.2 | 8.8 | 6.8 | 7.8 |
| Example 4 | 9.3 | 8.8 | 7.2 | 8.2 |
| Comp. ex. 1 | 31.2 | 6.8 | 4.3 | 8.2 |
| Comp. ex. 2 | 32.0 | 8.1 | 9.8 | 9.3 |
| Comp. ex. 3 | 21.2 | 6.8 | 10.6 | 22.7 |
| Comp. ex. 4 | 19.9 | 6.8 | 30.1 | 41.5 |

As the results of Table 2 reveal, no significant difference in POV, even after storage for 7 days in an environment at 40° C., was observed in Examples 1 to 4 or Comparative example 1 and 2. The samples were found to have high oxidation stability, since the peroxide value exhibited no significant increase.

Test Example 3

To 18 g of each sample obtained in Examples 1 to 4 and Comparative examples 1 to 4 there were added 11.7 g of Dilactose S (by Freund Corporation) and 0.3 g of calcium stearate (by Taihei Chemical Industrial Co., Ltd.), with mixing of the whole. Tableting was then performed using a desk tableting machine HANDTAB-100 (by Ichihashi Seiki Co., Ltd.) at a tableting pressure of 10 kN, to yield oily substance-containing tablets having a diameter of 10 mm and a weight of 300 mg per tablet. Lamination incidence and tablet hardness were measured in the obtained tablets. The results are given in Table 3.

(7) Lamination Incidence

Lamination incidence was visually checked as the number of laminated tablets occurring in 10 obtained tablets.

(8) Tablet Hardness

The average value of tablet hardness for 10 tablets, obtained using a load cell-type tablet hardness tester/portable checker PC-30 (by Okada Seiko Co., Ltd.), was taken herein as the tablet hardness.

TABLE 3

|  | Lamination incidence (%) | Tablet hardness (N) |
| --- | --- | --- |
| Example 1 | 0 | 77 |
| Example 2 | 0 | 50 |
| Example 3 | 0 | 65 |
| Example 4 | 0 | 74 |
| Comp. ex. 1 | 20 | 21 |
| Comp. ex. 2 | 40 | 30 |
| Comp. ex. 3 | 0 | 45 |
| Comp. ex. 4 | 0 | 9 |

The results of Table 3 reveal that no defective tableting in the form of lamination or the like occurs in the tablets of Examples 1 and 2, in which tablet hardness takes on a high value of 40 N or higher (in particular 50 N or higher). By contrast, lamination occurs in Comparative examples 1 and 2, which exhibit also low tablet hardness.

The above results indicate that higher oxidation stability and moldability can be achieved when using the composition of the present invention. In Comparative examples 1 and 2, by contrast, lamination occurs and tablet hardness is low, while in Comparative examples 3 and 4 oxidation stability is low, as set out in Table 2. The comparative examples are thus found to be inferior to the composition of the present invention.

INDUSTRIAL APPLICABILITY

The composition of the present invention can be suitably used, with a focus on the pharmaceutical and foodstuff fields, for instance in drugs and quasi-drugs, and also in various supplements (functional foods, health supplements, nutrients and the like).

The invention claimed is:

1. A powder composition containing an oily substance, the powder composition comprising a powdery calcium silicate-based material and an oily substance impregnated into the material, wherein the powdery calcium silicate-based material comprises porous particles having pores of a size ranging from 10 to 70 nm and pores of a size ranging from 70 to 500 nm, and wherein, in the material, a cumulative pore volume for pores of a pore size of 10 to 70 nm is 1.1 cc/g or more and a cumulative pore volume for pores of a pore size of 70 to 500 nm is 2.0 cc/g or less.

2. The powder composition containing an oily substance according to claim 1, wherein the oily substance is at least one type from among 1) at least one of docosahexaenoic acid (DHA) and eicosapentaenoic acid (EPA), 2) an edible natural oil containing the DHA and/or the EPA, and 3) a refined oil of the edible natural oil.

3. The powder composition containing an oily substance according to claim 1, having an average particle diameter of 1 to 50 μm.

4. The powder composition containing an oily substance according to claim 1, wherein the content of the oily substance in the composition is 30 wt % or higher.

5. A molded body obtained through compression molding of the composition containing an oily substance according to claim 1.

* * * * *